United States Patent [19]

Hiramoto et al.

[11] Patent Number: 4,826,280
[45] Date of Patent: May 2, 1989

[54] GROOVED OPTICAL TRANSMISSION CHANNEL

[75] Inventors: Jun-ichi Hiramoto; Koichi Tsuno, both of Osaka, Japan

[73] Assignee: Sumitomo Electric Industries, Ltd., Osaka, Japan

[21] Appl. No.: 149,898

[22] Filed: Jan. 28, 1988

Related U.S. Application Data

[63] Continuation of Ser. No. 615,533, May 31, 1984, abandoned.

[30] Foreign Application Priority Data

Jun. 9, 1983 [JP]  Japan ............................... 58-103940

[51] Int. Cl.⁴ .......................... G02B 23/26; G02B 6/04
[52] U.S. Cl. ............................... 350/96.26; 350/96.24; 350/96.34
[58] Field of Search ............... 350/96.23, 96.24, 96.25, 350/96.26, 96.34

[56] References Cited

U.S. PATENT DOCUMENTS

| | | | |
|---|---|---|---|
| 3,261,349 | 7/1969 | Wallace | 350/96.26 X |
| 3,434,775 | 3/1969 | Gosselin | 350/96.26 |
| 3,776,222 | 12/1973 | Smiddy | 350/96.26 X |
| 4,173,392 | 11/1979 | Ekinaka et al. | 350/96.26 |
| 4,181,397 | 1/1980 | Baker et al. | 350/96.26 X |
| 4,184,743 | 1/1980 | Baker et al. | 350/96.26 X |
| 4,325,606 | 4/1982 | Ikuno et al. | 350/96.26 X |
| 4,341,205 | 7/1982 | Hosono et al. | 350/96.26 X |
| 4,593,973 | 6/1986 | Yoshida et al. | 350/96.25 X |

FOREIGN PATENT DOCUMENTS

| | | | |
|---|---|---|---|
| 0035343 | 3/1980 | Japan | 350/96.26 |
| 0011426 | 2/1981 | Japan | 350/96.26 |

Primary Examiner—William L. Sikes
Assistant Examiner—Akm E. Ullah
Attorney, Agent, or Firm—Wenderoth, Lind & Ponack

[57] ABSTRACT

An optical transmission channel for use in such optical devices as a fiberscope or an optical fiber sensor. The optical transmission channel is formed of an optically transmissive material and extends longitudinally with a substantially cylindrical peripheral surface. At least one groove extends parallel to the axis of the channel in the peripheral surface and provides an efficient space for receiving another optically transmissive member. In a preferred embodiment, a fiberscope includes a grooved illuminating light transmission channel having an image fiber mounted in one groove and a tube mounted in the other, the tube being provided to carry air between a balloon member at one end and a syringe at the other for contracting and expanding the balloon. By providing the tube and image fiber in grooves in the illuminating light transmission channel, the required cross-sectional area for these elements may be minimized.

5 Claims, 2 Drawing Sheets

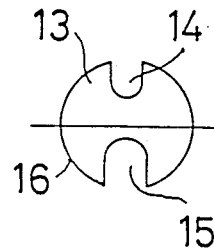
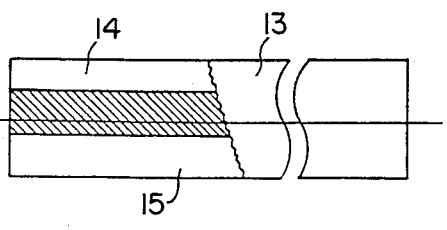
FIG. 4A  FIG. 4B
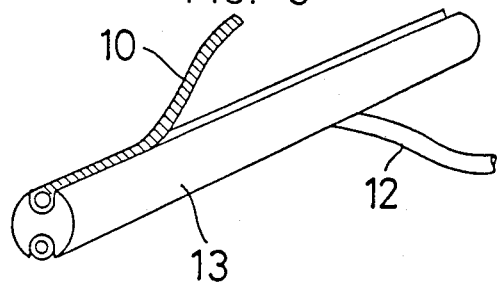
FIG. 5
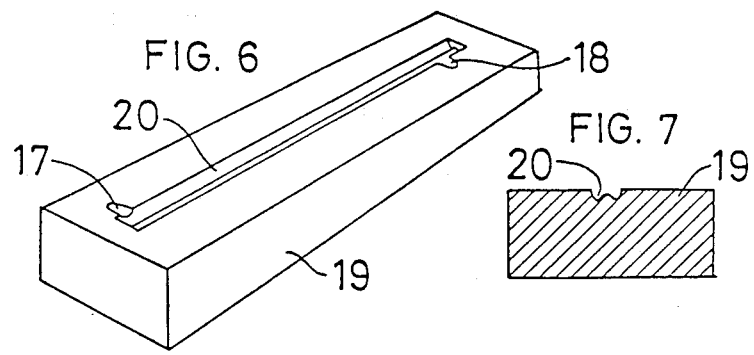
FIG. 6  FIG. 7

GROOVED OPTICAL TRANSMISSION CHANNEL

This application is a continuation of now abandoned application Ser. No. 615,533, filed May 31, 1984.

BACKGROUND OF THE INVENTION

The present invention relates to a structure of an optical transmission channel for use in a fiberscope, an optical fiber sensor and the like, having an illuminating light transmission channel, an information light transmission channel and various kinds of auxiliary transmission channels.

The conventional optical transmission channel for use in a fiberscope for making observations in a heart and blood vessels, as disclosed in Japanese Laid-Open Patent No. 55-151936 (1980) titled "Internal Observation Apparatus", requires special features because the heart and blood vessels are filled with an opaque liquid i.e. blood.

Referring now to FIG. 1, a flexible cable portion 4 of a fiberscope encloses illuminating light transmission fibers and an information light transmission image fiber (image direct-transmission fiber optics, and a transparent balloon 3 is provided at a pointed head thereof in order to observe the internal wall 1 of a heart.

The balloon 3 is flexible and can when bulged displace blood 2, which obstructs the field of vision in front of the fiberscope thereby permitting observation of the internal wall 1 of a heart.

Reference numeral 6 designates an image-receiving adaptor for observing transmitted images, reference numeral 8 designates a light source of an illuminating light, and reference numeral 9 designates a syringe for expanding and contracting said balloon 3.

In prior fiberscopes the flexible cable portion 4 as shown in section in FIG. 2, has four illuminating light transmission plastic fibers 11 arranged around an image fiber 10 and a tube 12 for expanding and contracting said balloon 3, housed in said flexible cable portion 4.

However, an optical transmission channel according to the above described conventional art has the following disadvantages:

(1) Large gaps are formed among said image fiber 10, said plastic fibers 11 and said tube 2 and thus the cross-sectional area of said flexible cable portion 4 is inefficiently utilized since said image fiber 10, said plastic fibers 11, said tube 12 have circular cross sections and they are housed in said flexible cable portion 4 also having a circular cross section.

(2) The labor costs for collecting and branching of the fibers and tube are high.

BRIEF SUMMARY OF THE INVENTION

It is an object of the present invention to provide an optical transmission channel which can solve the disadvantages incidental to the conventional optical transmission channels by improving the efficiency of use of the cross-sectional area of the cable and facilitating easy collecting and branching of the fibers and tube.

In accordance with the present invention, there is provided an optical transmission channel which includes an optically transmissive member which may form an illuminating light transmission channel, having a substantially cylindrical peripheral surface surrounding its longitudinal axis, the peripheral surface having at least one groove therein extending parallelly to the axis for receiving at least a second optically transmissive member. In the preferred embodiment, the optical transmission channel is provided in a fiberscope and an image fiber is provided in the groove in an illuminating light transmission channel within a cable which can be extended through blood vessels into a human heart. By providing the second light transmissive member in a groove in the first, the assembly is made easy, and the overall cross-sectional area of the device is minimized.

BRIEF DESCRIPTION OF THE DRAWINGS

The present invention will be described in detail below with reference to the drawings illustrating a preferred embodiment of the present invention, in which FIG. 5 is a diagram illustrative of a procedure for assembling an optical transmission channel according to the present invention, FIG. 6 is a perspective view of a metallic mold for forming an optical transmission channel according to the present invention, and FIG. 7 is a cross-sectional view of the metallic mold shown in FIG. 6.

DETAILED DESCRIPTION OF THE PREFERRED EMBODIMENTS

Figure 1:
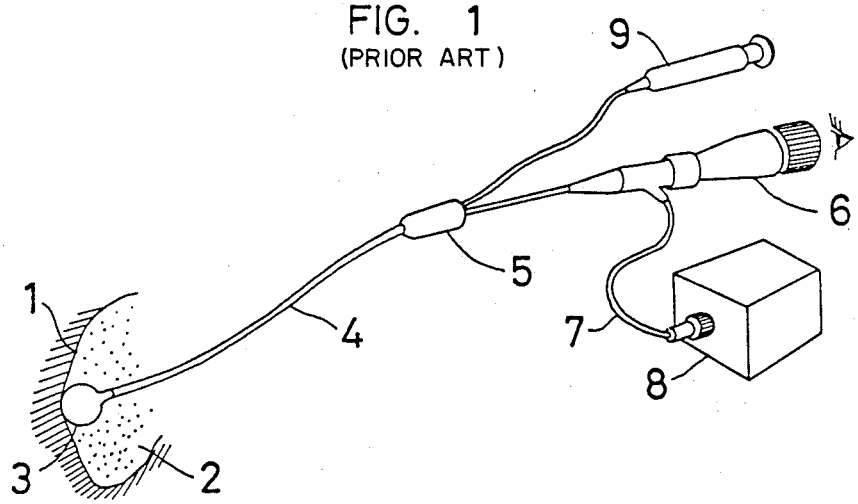
FIG. 1 is a diagram showing an example of the structure of a conventional fiberscope for viewing the heart and blood vessels.
Figure 2:
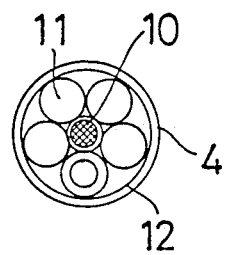
FIG. 2 is a sectional view showing a sectional structure of the conventional fiberscope shown in FIG. 2.
Figure 3:
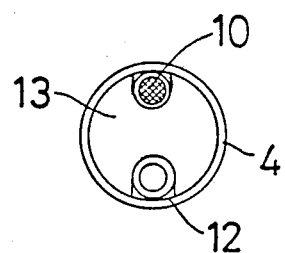
FIG. 3 is a sectional view showing a sectional structure of a fiberscope using an optical transmission channel according to the present invention, FIGS. 4(A) and (B) represents two diagrams showing a structure of an optical transmission channel according to the present invention.

Referring now to FIG. 3, a section of a grooved optical transmission channel 13 according to the present invention occupies all of a flexible cable portion 4 except for the space occupied by an image fiber 10 and a tube 12 for controlling the balloon.

As shown in FIGS. 4(A) and (B), said grooved optical transmission channel 13 for illuminating light transmission is provided with a groove 14 for receiving the image fiber 10 and a groove 15 for receiving the tube 12 for controlling the balloon. Both grooves are provided in parallel to an axis of the channel 13 on the circumference thereof.

As shown in FIG. 5, said grooves 14, 15 make the collecting operation and branching operation of said image fiber and said tube 12 for controlling the balloon easy.

In addition, said optical transmission channel can be produced in a two-segment type metallic mold 19 as shown in FIG. 6 (only one segment being shown in the figure). A groove 20 in the metallic mold has a section as shown in FIG. 7 and is filled with transparent materials such as PMMA (polymethylmethacrylate), PiBMA (polyisobutylmethacrylate), PnBMA (polynormal-butylmethacrylate), polystyrene, polycarbonate and silicic rubber by means of a filling port 17 and an overflow port 18. In addition, it is necessary that the external surface of the obtained grooved optical transmission channel 13 is covered with a clad 16 (refer to FIG. 4)—a thin film of the materials having the refractive index smaller than that of said transparent materials. This film may be applied by an immersion or dipping method or the like and is provided in order to control the optical loss resulting from injuries produced in the assemblying operation.

According to the present invention, (1) The efficiency of utilization of the cross-sectional area of the cable portion is a fiberscope can be improved, and permit reduction of the diameter of an optical transmission channel as a whole (so as to be easily inserted into blood vessels and the like), provided that the cross-sectional area of the illuminating light transmission channel is constant.

(2) The collecting and branching of the fibers and the balloon control tube can be easily carried out.

A grooved optical transmission channel according to the present invention can be used in such applications as (1) illuminating light transmission channels of fiberscopes and (2) optical transmission channels of various kinds of fiber optic sensors.

What is claimed is:

1. An optical transmission channel comprising a one piece optically transmissive light guide member consisting of a transparent optical medium for transmitting light, said one piece member consisting of the optical medium having a longitudinal axis, and a generally cylindrical outer peripheral surface, said peripheral surface having at least one groove therein, said groove extending in a direction that is parallel to said axis, and said optical medium including at least one of PMMA (polymethylmethacrylate), PBMA (polyisobutylmethacrylate), PnBMA (polynormalbutylmethacrylate), polystyrene, polycarbonate and silicic rubber.

2. An optical transmission channel as set forth in claim 1, wherein said member has two longitudinally opposite ends and, said at least one groove extends from one of said two ends to the other of said two ends.

3. An optical transmission channel device comprising:

a one piece optically transmissive light guide member consisting of an optical medium for transmitting light, said one piece member consisting of the optical medium having a first end and a second end opposite said first end, a longitudinal axis extending between said first end and said second end, and a generally cylindrical outer peripheral surface, said peripheral surface having at least one groove extending therein from said first end to said second end in a direction that is parallel to said axis; and at least one other member each of which extends in a respective one of said at least one groove, said at least one other member comprising another optically transmissive member, said at least one other member having a cross-sectional area that is substantially equal to the cross-sectional area of the respective groove in which it extends such that said at least one other member only substantially fills said groove in which it extends.

4. A device as set forth in claim 3, wherein said first member comprises an illuminating light transmission channel and said other member comprises an image fiber.

5. A device as set forth in claim 4, wherein said at least one groove includes two grooves, and further comprising a longitudinally extending tube for carrying air from said first end to said second end extending in one of said two grooves, said image fiber being disposed in the other of said two grooves.

* * * * *